(12) United States Patent
Han et al.

(10) Patent No.: US 7,488,579 B2
(45) Date of Patent: Feb. 10, 2009

(54) METHODS AND COMPOSITIONS TO EXTRACT DNA, RNA AND PROTEIN SIMULTANEOUSLY FROM BIOLOGICAL SAMPLES

(75) Inventors: Xiaoliang Han, San Francisco, CA (US); Zhongdong Liu, Newark, CA (US); Jinming Xia, San Francisco, CA (US)

(73) Assignee: BioChain Institute, Inc., Hayward, CA (US)

( * ) Notice: Subject to any disclaimer, the term of this patent is extended or adjusted under 35 U.S.C. 154(b) by 348 days.

(21) Appl. No.: 10/839,905

(22) Filed: May 5, 2004

(65) Prior Publication Data

US 2004/0224344 A1    Nov. 11, 2004

Related U.S. Application Data

(60) Provisional application No. 60/468,555, filed on May 6, 2003.

(51) Int. Cl.
*C12Q 1/68* (2006.01)

(52) U.S. Cl. ......................................................... 435/6

(58) Field of Classification Search ....................... None
See application file for complete search history.

(56) References Cited

U.S. PATENT DOCUMENTS

| | | | | |
|---|---|---|---|---|
| 5,010,183 A | * | 4/1991 | Macfarlane | 536/25.4 |
| 5,346,994 A | * | 9/1994 | Chomczynski | 530/419 |
| 5,945,515 A | * | 8/1999 | Chomczynski | 530/412 |
| 6,043,354 A | * | 3/2000 | Hillebrand et al. | 536/25.42 |
| 6,204,375 B1 | * | 3/2001 | Lader | 536/25.4 |

OTHER PUBLICATIONS

Sambrook J et. al. Molecular Cloning vol. 1, pp. E.3, Cold Spring harbor Laboratory Press (1989).*

* cited by examiner

*Primary Examiner*—Teresa E Strzelecka
*Assistant Examiner*—Suchira Pande
(74) *Attorney, Agent, or Firm*—Junrui Yang; Joe Zheng

(57) ABSTRACT

This invention presents a set of methods to extract DNA, RNA and protein simultaneously from biomaterials by reagents with high pH. DNA and RNA can be extracted from a upper aqueous phase simultaneously either together as a DNA and RNA mixture or separated DNA and RNA. Protein can be extracted from lower organic phase. The DNA and RNA mixture can be used either as DNA or RNA directly depending on applications without further separation, or as resource for the separated DNA and RNA that can be selected from the DNA and RNA mixture by selective precipitation and/or by selective enzyme digestions. This invention provides the choice of extraction either of DNA and RNA mixture or of separated DNA and RNA simultaneously, as well as extraction of protein from the same piece of biomaterials in high quality, which is very critical for biomaterials with limited resource, such as clinical specimens.

14 Claims, 13 Drawing Sheets

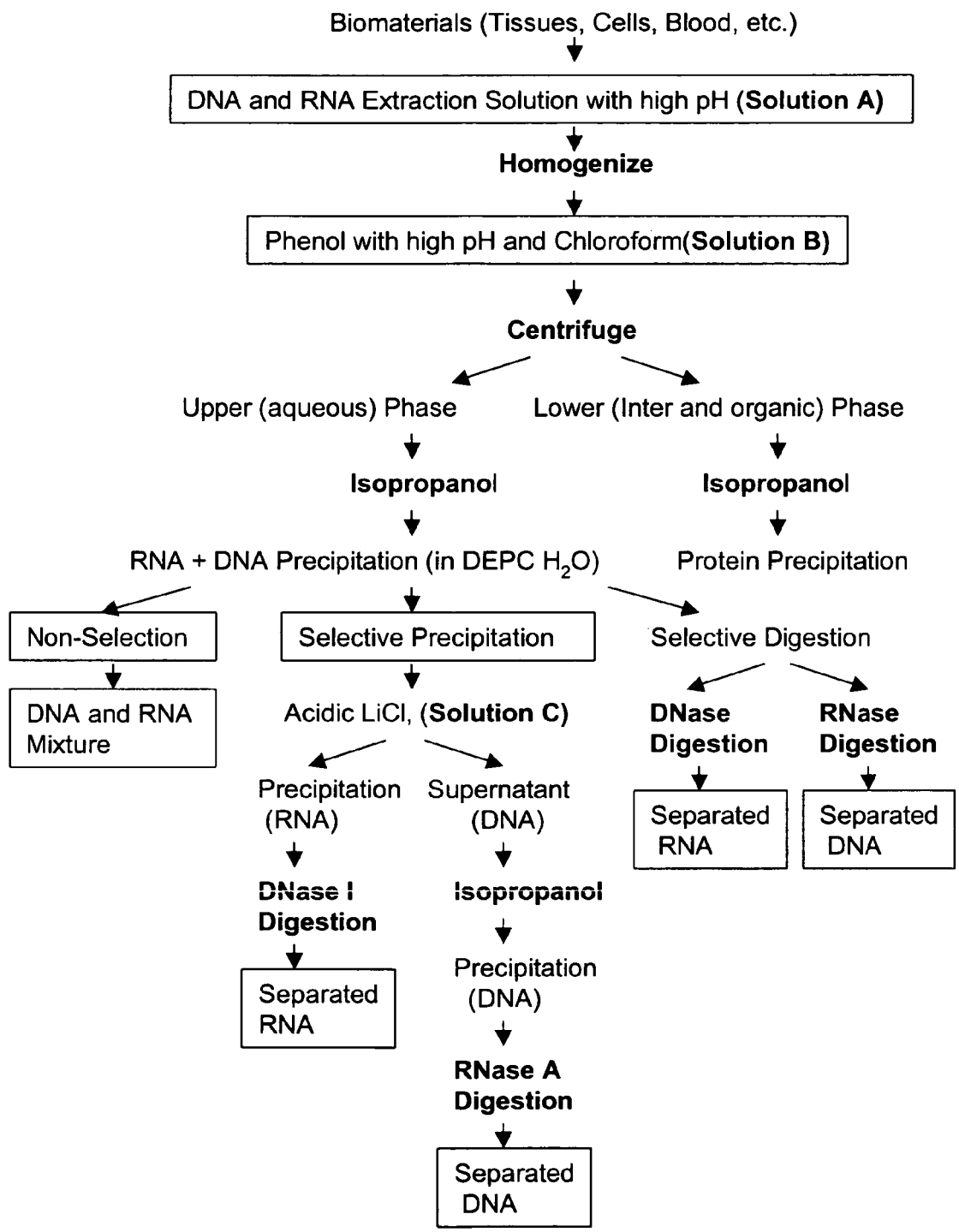
Fig. 1. Flow chart of Extracting DNA, RNA and Protein Simultaneously from Biomaterials

Fig. 2. Shift of DNA and RNA between Phases of Extraction Reagents with Different pH

|  | Low pH | | | | High pH | | | | |
|---|---|---|---|---|---|---|---|---|---|
| Upper | | Lower | | | Upper | | Lower | | |
| D | R | D | EP | IP | D | R | D | EP | IP |
| 1 | 2 | 3 | 4 | 5 | 6 | 7 | 8 | 9 | 10 |

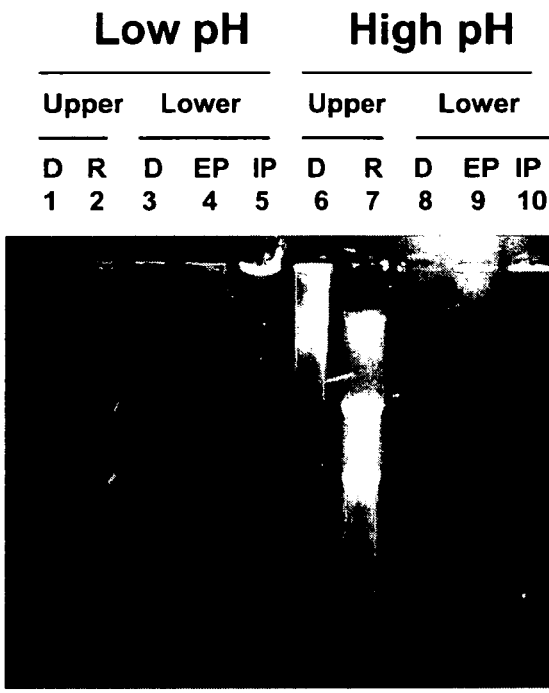

Lane 1. DNA in upper phase extracted at low pH, no DNA
Lane 2. RNA in upper phase extracted at low pH, less amount of RNA
Lane 3. DNA in lower phase extracted at low pH, some DNA
Lane 4. Protein in lower phase extracted at low pH, with ethanol pre-precipitation, less DNA contamination
Lane 5. Protein in lower phase extracted at low pH, without ethanol pre-precipitation, mass DNA contamination
Lane 6. DNA in upper phase extracted at high pH, large amount of DNA
Lane 7. RNA in upper phase extracted at high pH, large amount of RNA
Lane 8. DNA in lower phase extracted at high pH, less amount of DNA
Lane 9. Protein in lower phase extracted at high pH with ethanol pre-precipitation, less DNA contamination
Lane 10. Protein in lower phase extracted at high pH, without ethanol pre-precipitation, less DNA contamination

Fig. 3. Agarose gel Analysis of DNA and RNA mixture
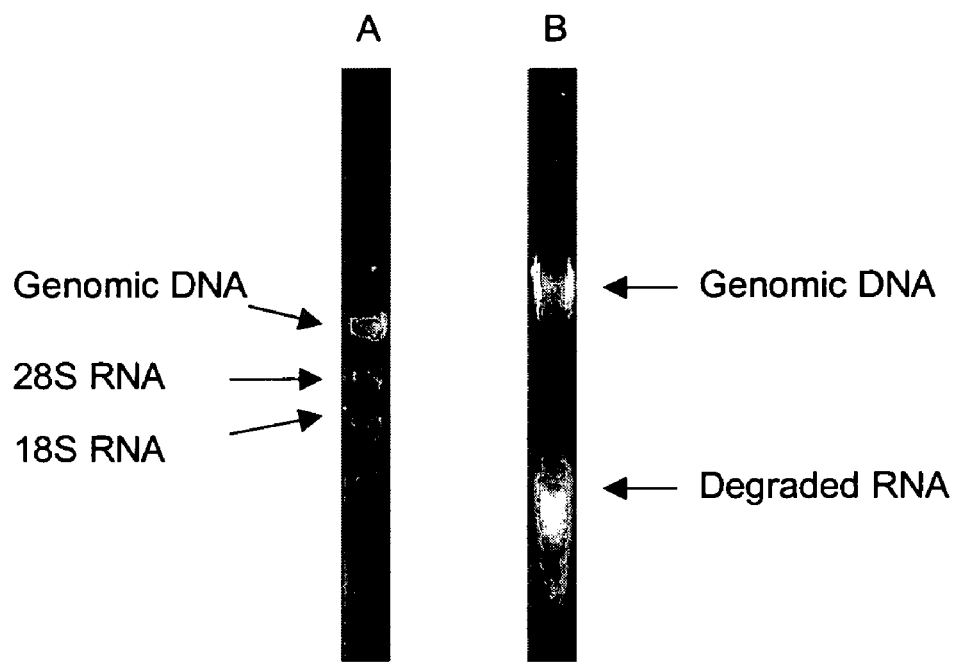
A) DNA and RNA mixture on denaturing agarose gel for RNA
B) DNA and RNA mixture on non-denaturing agarose gel for DNA

Fig. 4. Genomic DNA and RNA Separated by Selective Precipitation with LiCl

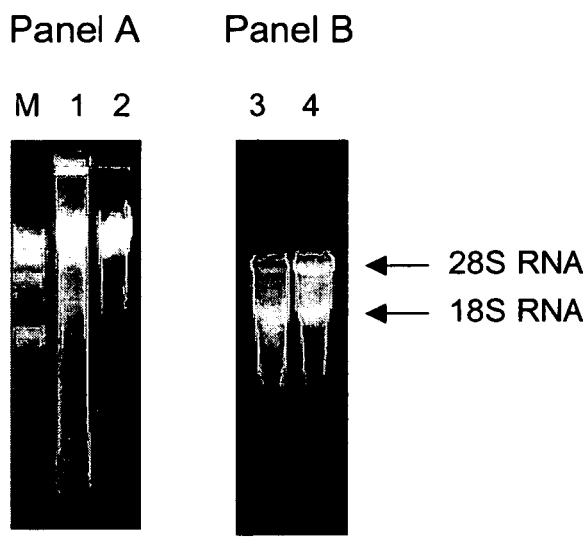

Panel A) Genomic DNA on non-denaturing agarose gel for DNA
  Lane M. DNA marker (Lambda phage digested by HindIII from Invitrogen)
  Lane 1. Genomic DNA extracted by conventional method (protease K )
  Lane 2. Separated DNA extracted by reagents with high pH and
    selective precipitation in this invention Panel B) Total RNA on denaturing agarose gel for RNA
  Lane 3. RNA extracted by reagents with low pH
  Lane 4. Separated RNA extracted by reagents with high pH
    and selective precipitation in this invention

Fig. 5. Genomic DNA and RNA Separated by Selective Enzyme Digestion

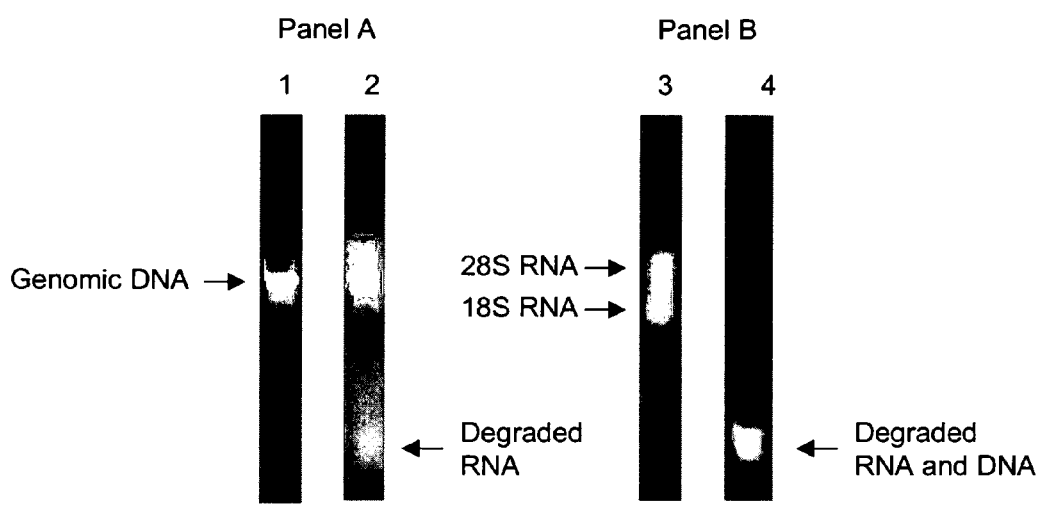

Panel A)
Electrophoresis of Genomic DNA extracted by reagents with high pH and selective enzyme digestion with RNase
        Lane 1. In non-denaturing argarose gel for DNA
        Lane 2. In denaturing agarose gel for RNA Panel B)
Electrophoresis of Total RNA extracted by reagents with high pH and selective enzyme digestion with DNase
        Lane 3. In denaturing agarose gel for RNA
        Lane 4. In non-denaturing argarose gel for DNA

Fig. 6. Comparison Between Proteins Extracted by Reagents with low pH and high pH

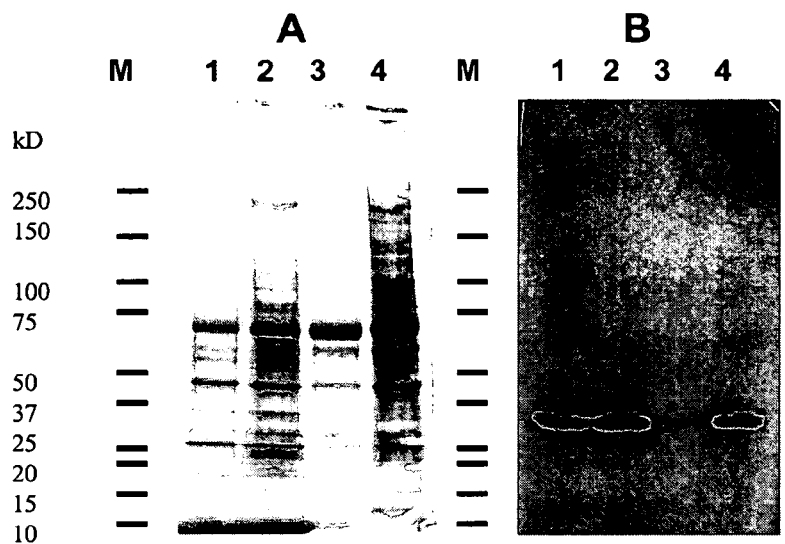

Panel A. SDS-PAGE of proteins
Panel B. Western blotting analysis protein in panel A with anti-GAPDH antibody Lane M. Protein Standards for molecular weight
(Precision Plus from BioRad Cat# 161-0374)
Lane 1. Protein extracted from 0.1 mg Human Spleen tissue by conventional methods without extraction by organic reagents.
Lane 2. Protein extracted from 0.2 mg Human Spleen tissue by conventional methods without extraction by organic reagents.
Lane 3. Protein extracted from 0.2 mg Human Spleen tissue from lower phase by reagents with low pH Lane.
4. Protein extracted from 0.2 mg Human Spleen tissue from lower phase by reagents with high pH in this invention.

Fig. 7. PCR Analysis of DNA and RNA with Different Separation Methods

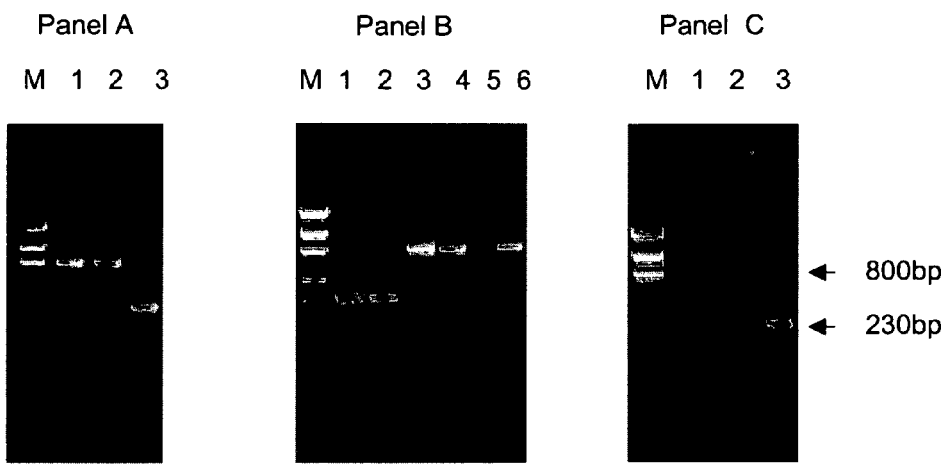

Panel A: PCR with DNA and RNA mixture without separation
Lane M. DNA marker (Low DNA Mass ladder from Invitrogen)
Lane 1. PCR product of EGFR gene from DNA and RNA mixture without RT reaction
Lane 2. RT-PCR product of EGFR gene from DNA and RNA mixture
Lane 3. RT-PCR product of EGFR gene from control RNA Panel B: PCR with separated DNA and RNA by selective precipitation
Lane M. DNA marker (Low DNA Mass ladder from Invitrogen)
Lane 1. RT-PCR product of EGFR gene from separated RNA without further DNase digestion
Lane 2. RT-PCR product of EGFR gene from separated RNA with further DNase digestion
Lane 3. RT-PCR product of EGFR gene from separated DNA without further RNase digestion
Lane 4. RT-PCR product of EGFR gene from separated DNA with further RNase digestion
Lane 5. RT-PCR product of EGFR gene from control RNA
Lane 6. RT-PCR product of EGFR gene from control genomic DNA Panel C: PCR with separated DNA and RNA by selective enzyme digestion
Lane M. DNA marker (Low DNA Mass ladder from Invitrogen)
Lane 1. RT-PCR product of EGFR gene from control genomic DNA
Lane 2. RT-PCR product of EGFR gene from separated genomic DNA
Lane 3. RT-PCR product of EGFR gene from separated RNA

Fig. 8. Qualitative Comparison between RNA extracted by Reagents with High or Low pH

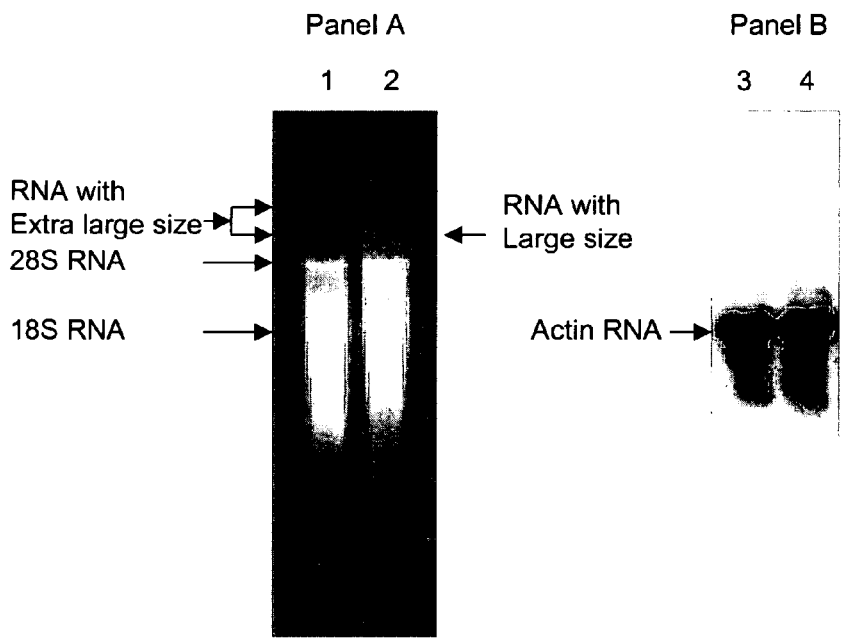

Panel A Electrophoresis of Total RNA in denaturing agarose gel for RNA
Lane 1. RNA extracted by reagents with high pH and selective precipitation with further DNase digestion, showing extra populations of RNA with extra large size
Lane 2. RNA extracted by reagents with low pH and and selective precipitation with further DNase digestion Panel B Hybridization of RNA on Northern blot made from gel in Panel A
Lane 3. RNA in lane 1 of Panel A
Lane 4. RNA in Lane 2 of Panel A

Fig. 9. Comparison of cDNA made from RNA Extracted by Reagents with High or Low pH

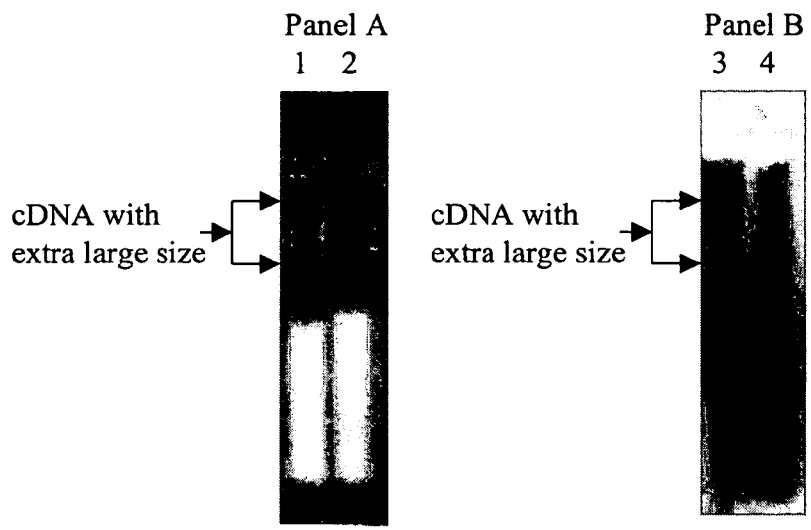

Panel A cDNA visualized by dye staining inside agarose gel
Lane 1. cDNA made by RNA extracted by reagents with high pH and selective precipitation with further DNase digestion, showing extra population of cDNA with extra large size.
Lane 2. cDNA made by RNA extracted by reagents with low pH as conventional method.

Panel B cDNA visualized by exposing detectable marker on cDNA to film
Lane 3. selective precipitation with further DNase digestion, showing extra population of cDNA with extra large size.
Lane 4. cDNA made by RNA extracted by reagents with low pH as conventional method.

Fig. 10. Protein Contamination in DNA and RNA Extracted by Reagent with low pH

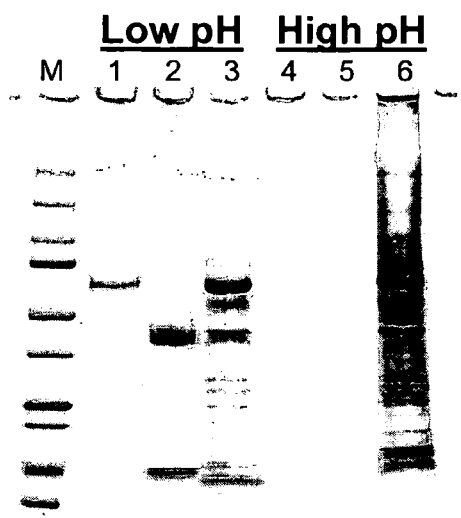

SDS-PAGE of DNA, RNA and protein extracted from upper or lower phase by reagents with low or high pH Lane M. Protein Standards for molecular weight (Precision Plus from BioRad Cat# 161-0374)
Lane 1. DNA extracted from lower phase by reagents with low pH, see protein contamination
Lane 2. RNA extracted from upper phase by reagents with low pH, see protein contamination
Lane 3. Protein extracted from upper phase by reagents with low pH
Lane 4. DNA extracted from upper phase by reagents with high pH
Lane 5. RNA extracted from upper phase by reagents with high pH
Lane 6. Protein extracted from lower phase by reagents with low pH

Fig. 11. Endurance to DNAse Treatment for the RNA Extracted by Reagents with High or Low pH

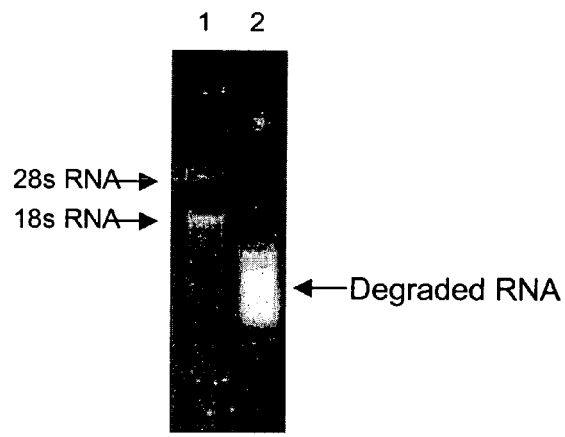

Lane 1. RNA extracted by reagents with high pH and selective precipitation followed by further teatment of DNase digestion. No degradation of RNA
Lane 2. RNA extracted by organic reagents with low pH and further treated with DNase digestion. RNA is degraded after DNase treatment.

Fig. 12. Shifting between Phases and Gel Electrophoresis of DNA extracted by Reagents with Low or High pH

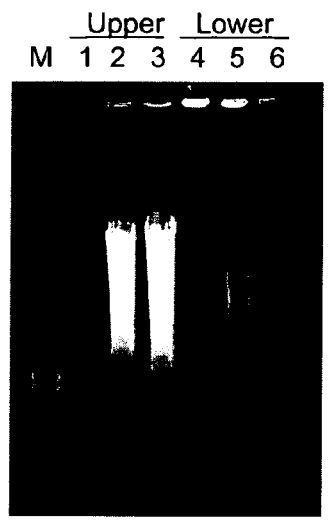

Agarose gel electrophoresis of DNA extracted from upper(aqueous) phase and lower (inter and organic phase) phase by reagents with low or high pH.
Lane M is DNA marker (Lamda phage digested by HindIII from Invitrogen).
Lane 1 is DNA extracted from upper phase by reagents with low pH and selective precipitation. Little DNA exists;
Lane 2 is DNA extracted from upper phase by reagents with neutral pH and selective precipitation. DNA presents in large amount and is proper for gel electrophoresis;
Lane 3 is DNA extracted from upper phase by reagents with high pH and selective precipitation. DNA presents in large amount and is proper for gel electrophoresis;
Lane 4 is DNA extracted from lower phase by reagents with low pH. Some amount of DNA presents but stuck in gel well during electrophoresis;
Lane 5 is DNA extracted from lower phase by reagents with neutral pH. Some amount of DNA presents but stuck in gel well during electrophoresis;
Lane 6 is DNA extracted from lower phase by reagents with high pH. Only little DNA existed but stuck in gel well during electrophoresis.

Fig. 13. Qualitative Comparison between DNA Extracted by Reagents with High or Low pH

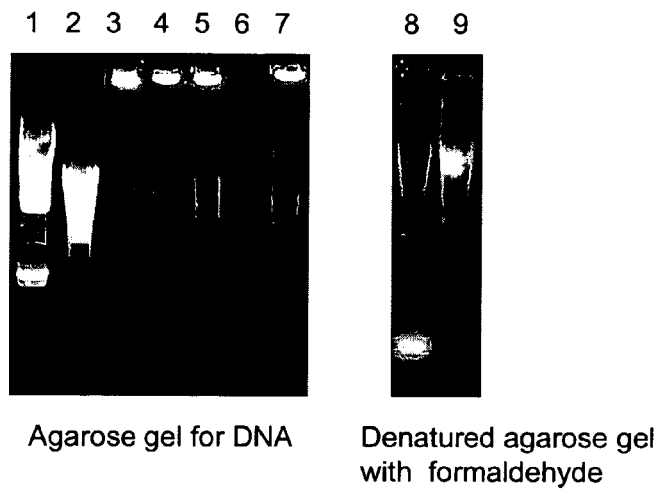

Agarose gel for DNA     Denatured agarose gel with formaldehyde

Lane 1 to 7. DNA electrophoresis in non-denaturing agarose gel for DNA.
Lane 1. DNA marker (Lamda phage digested by HindIII from Invitrogen)
Lane 2. DNA extracted from upper phase by reagents with high pH
Lane 3. DNA extracted from lower phase by reagents with low pH
Lane 4. DNA extracted from lower phases and treated with ethanol wash.
Lane 5. DNA extracted from lower phases and treated with phenol extraction
Lane 6. DNA extracted from lower phases and treated with Dnase digestion
Lane 7. DNA extracted from lower phases and treated with HindIII digestion Lane 8 to 9. DNA electrophoresis in denatured agarose gel with formaldehyde.
Lane 8. DNA extracted from upper phase by reagents with high pH
Lane 9. DNA extracted from lower phases by reagents with low pH

METHODS AND COMPOSITIONS TO EXTRACT DNA, RNA AND PROTEIN SIMULTANEOUSLY FROM BIOLOGICAL SAMPLES

REFERENCE TO RELATED APPLICATION

This application claims the benefit of the provisional application filed on May 6, 2003, Ser. No. 60/468,555, by the same inventors.

BACKGROUND OF THE INVENTION

As the Human Genome Project and other genome sequencing efforts are completed, the demand for various Deoxyribonucleic acid (DNA), ribonucleic acid (RNA) and protein has been increased in a great deal from life science researchers. For example, RNA extraction is required to compare differentially expressed gene between normal tissues and tumor tissues, or between tumor cells and drug treated tumor cells. Also, human genome profiling and gene expression profiling require the comparison of DNA, RNA and protein from the same piece of biomaterials. Extraction of high quality DNA, RNA and protein simultaneously without cross contamination are very difficult, especially when the biological samples are very limited. For example, amounts of clinical specimens are so small that it is impossible for life science researchers to divide them into even smaller sections to extract DNA, RNA and protein separately.

There is no appropriate or dependable technique for isolation of DNA, RNA and protein simultaneously from biological samples. Cesium chloride (CsCl) gradient is a traditional method for extracting DNA and RNA at the same time, but no protein is extracted. Very few people are using this method for RNA and DNA extraction because of its time consuming and high expense. Column purification of RNA and DNA from tissue without protein is another method but the yield is relative low and some populations of RNA and DNA are lost.

A commercial kit method claims that it can extract DNA, RNA and protein from biomaterials at the same time with acidic phenol or acidic extraction (low pH) reagents (U.S. Pat. No. 5,346,994). However, the major application of this method is designed to extract RNA only because the quality of DNA and protein is so poor that they cannot be used in any real application as DNA and protein are intended to be. In this methods DNA is moved into organic phase of extraction by reagents with low pH (or acidic extraction reagents) in order to separate DNA and RNA, while RNA stays in aqueous phase. But this kit method has to pay tremendous sacrifices for losing the populations of RNA with large size as these populations of RNA moved into organic phase along with DNA, thereby causing substantial contamination to DNA due to the presence of protein or unknown materials to be used, such that the entirety of protein population is lost so much that protein cannot be used in almost any applications. The procedures of this kit method with acidic extraction reagents are described briefly as follows: biomaterials are homogenized in these acidic extraction reagents, in addition of chloroform extraction followed by centrifugation, the homogenate will be separated in three phases: aqueous phase, inter phase and organic phase. RNA stays in the aqueous phase, DNA and protein are in the inter phase and organic phase. Further process on inter phase and organic phase can separate DNA and protein. Then DNA, RNA and protein can be isolated respectively.

Although the kit method with acidic extraction reagent gives RNA with acceptable quality from cell lines, the quality of DNA, RNA and protein extracted from biomaterials, especially primary tissues, are very compromised compared with the other conventional extraction methods, such as CsCl gradient centrifugation, protease K digestion for DNA extraction, and non-ionic detergent for protein extraction. loosing large molecules of DNA, RNA and protein and decreasing recovery rate of DNA and protein DNA and protein indicate that some population of DNA, RNA and protein are lost from the extraction by reagents with low pH used in commercial kit. The lacking of stability, purity and some populations of the DNA, RNA and protein extracted by reagents with low pH as used in kit method, especially from tissues, are serious problems. One of such example is when these DNA, RNA and protein are used in gene expression profiling that becomes more and more demanding in terms of completed and representative populations of DNA, RNA and protein. Other major drawback to prevent users from using this kit method to extract DNA, RNA and protein simultaneously is that processes are too complicated to carry on, especially to extract DNA and protein.

Poor qualities of DNA, RNA and protein extracted by reagents with low pH as used in kit method are caused by several reasons. First, pre-mixture of denaturing reagents such as Guanidine and phenol can lead to incomplete denaturing RNase existing in biomaterials, which degrades RNA during processes afterward. Second, extraction by reagents with low pH moves only a portion of genomic DNA into organic phase, which causes lower yield of DNA in later extraction; furthermore, extraction by reagents with low pH also moves some populations of RNA with extra large molecular weight (size) into organic phase, which reduces the yield of RNA population with extra large molecular weight (size). Third, DNA and protein may tangle together each other in organic phase to prevent DNA and protein from further separation. For instance, separation of DNA and protein in organic phase with ethanol could precipitate and lose protein with extra large molecular weight (size) and certain populations of protein (fragment of membranes) in pellet of DNA; in addition, DNA could not be precipitated completely from organic phase with lower concentration of ethanol, which decreases the yield of DNA. Fourth, isolations of DNA and protein involve many complicated steps with harsh conditions, which could break down the molecules of DNA and protein. Any one or any combination of four reasons described above will badly compromise the qualities of DNA, RNA and protein extracted by reagents with low pH as used in kit method.

SUMMARY OF THE INVENTION

This invention presents a set of methods to extract DNA, RNA and protein simultaneously from biomaterials by reagents with high pH. DNA and RNA can be extracted from upper (aqueous) phase simultaneously either together as a DNA and RNA mixture or separated DNA and RNA. Protein can be extracted from lower (inter phase and organic phase) phases. The DNA and RNA mixture can be used either as DNA or RNA directly depending on applications without further separation, or as resource for the separated DNA and RNA that can be selected from the DNA and RNA mixture by selective precipitation and/or by selective enzyme digestions. A product is developed based on this method. The product contains extraction reagents for DNA, RNA and protein, selective precipitation reagents and/or selective digestion reagents. This invention provides the choice of extraction either of DNA and RNA mixture or of separated DNA and RNA simultaneously, as well as extraction of protein from the same piece of biomaterials, which is very critical for biomaterials with limited resource, such as clinical specimens. High quality DNA, RNA and protein can be extracted from biomaterials by this invention.

BRIEF DESCRIPTION OF DRAWINGS AND FIGURES

FIG. 1 Flow chart of Extracting DNA, RNA and Protein Simultaneously from Biomaterials DNA, RNA and protein are extracted from biomaterials by extraction reagents with high pH. DNA and RNA are isolated from upper (aqueous) phase. Protein is isolated from lower (inter phase and organic phase) phase.

FIG. 2. Shift of DNA and RNA between Phases of Extraction Reagents with Different pH This figure shows the image of agarose gel electrophoresis of DNA, RNA and protein. DNA, RNA and protein are extracted by reagents with either low pH or high pH. DNA is extracted from upper phase and lower phase, RNA is extracted from upper phase, and protein is extracted from lower phase FIG. 3 Agarose gel Analysis of DNA and RNA mixture DNA and RNA mixture are isolated from human liver tissue and applied on agarose gel electrophoresis. Panel A shows image of DNA and RNA mixture on denaturing agarose gel for RNA. Panel B shows image of DNA and RNA mixture on agarose gel for DNA.

FIG. 4 Genomic DNA and RNA Separated by Selective Precipitation with LiCl

Genomic DNA and RNA in DNA and RNA mixture from human liver tissue are separated by selective precipitation with LiCl. Panel A shows the results of gel electrophoresis of genomic DNA. Lane M is DNA marker from Invitrogene with largest size of DNA marker at 23 kbp. Results of denaturing agarose gel electrophoresis of RNA are shown in Panel B.

FIG. 5 Genomic DNA and RNA Separated by Selective Enzyme Digestion

Genomic DNA and RNA in DNA and RNA mixture are separated by selective enzyme digestion with RNase and DNase. Panel A shows the results of gel electrophoresis of the separated genomic DNA. Results of gel electrophoresis of the separated RNA are shown in Panel B.

FIG. 6. Comparison Between Proteins Extracted by Reagents with low pH and high pH Panel A shows the results of polyacrylamide gel electrophoresis (PAGE) of the protein isolated by different method. Panel B. Western blotting analysis protein in panel A with anti-GAPDH antibody.

FIG. 7. PCR Analysis of DNA and RNA with Different Separation Methods DNA and RNA isolated by this invention are tested in RT-PCR (Polymerase Chain Reaction after Reverse Transcription of RNA) of EGFR (Epidermal Growth Factor Receptor) genomic DNA and RNA.

DNA and RNA mixture is in Panel A, separated DNA and RNA are in Panel B and Separated DNA and RNA are in Panel C.

FIG. 8. Qualitative Comparison between RNA extracted by Reagents with High or Low pH Results of gel electrophoresis are shown in Panel A and results of hybridization of RNA from this gel are shown in Panel B.

FIG. 9 Comparison of cDNA made from RNA Extracted by Reagents with High or Low pH cDNA is visualized by dye staining cDNA inside agarose gel in Panel A, or by exposing detectable marker on cDNA to film in Panel B.

FIG. 10. Protein Contamination in DNA and RNA Extracted by Reagent with low pH

Figure shows the image of SDS-PAGE of DNA, RNA and protein extracted from aqueous or lower phase by organic reagents with low or high pH.

FIG. 11. Endurance to DNase Treatment for the RNA Extracted by Reagents with High or Low pH RNA after DNase treatment is applied in electrophoresis of denaturing agarose gel.

FIG. 12. Shifting between Phases and Gel Electrophoresis of DNA extracted by Reagents with Low or High pH Agarose gel electrophoresis of DNA extracted from aqueous phase and lower phase by organic reagents with low or high pH.

FIG. 13. Qualitative Comparison between DNA Extracted by Reagents with High or Low pH Qualities of DNA are compared between DNA extracted by selective precipitation from aqueous phase by organic reagents with high pH in this invention and DNA extracted from lower phases by organic reagents with low pH as in conventional method for DNA isolation.

DETAILED DESCRIPTION OF THE INVENTION

Definition used in this application:

Low pH is pH value less than 7. Neutral pH is pH value about 7. High pH is pH more than 7. Aqueous phase is water-soluble phase. Organic phase is water-non-soluble phase. Inter phase is the phase between water-soluble phase and water-non-soluble phase. Upper phase is aqueous phase or water-soluble phase. Lower phase is organic phase and Inter phase, or water-non-soluble phase and the phase between water-soluble phase and water-non-soluble phase. Conventional methods are well-accepted or standard methods that have been used by many people. Kit method is a conventional method using acidic reagents for extraction DNA, RNA and protein. DNA and RNA mixture is specimen containing both DNA and RNA. Separated DNA is specimen containing only DNA separated from DNA and RNA mixture. Separated RNA is specimen containing only RNA separated from DNA and RNA mixture.

To concur the problems of poor qualities of DNA, RNA and protein extracted by reagents with low pH as used in kit method, this invention present a method to address and correct above four issues. Denaturing reagents such as Guanidine Thiocyanate solution and phenol solution are separated apart during extraction to maximize the ability of denaturing RNases, DNases and proteases. Reagents with high pH (neutral or alkaline extraction solutions) instead of reagents with low pH (acidic extraction solutions) are used to retain DNA and RNA in aqueous phase to increase recovery of total populations of DNA and RNA including molecules with extra large size, which also helps complete recovery of protein populations including molecules with extra large size since interference of separating DNA from protein in organic phase is eliminated. Genomic DNA is extracted from aqueous phase in this invention instead of from organic phase. Therefore, the procedures of extraction by reagents with low pH are simplified to minimize the harsh conditions and treatments on DNA, RNA and protein molecules.

DNA, RNA and protein are extracted simultaneously from biomaterials by reagents with high pH in this invention. Both DNA and RNA can be extracted simultaneously as a mixture, or as separated DNA or RNA from upper (aqueous) phase.

Protein is extracted from lower phase (including inter phase and organic phase). The DNA and RNA mixture can be either used as DNA or RNA directly depended on applications without further separation, or as resource for the separated DNA and RNA that can be isolated from DNA and RNA mixture simultaneously either by selective precipitation followed with or without selective enzyme digestions, or by selective enzyme digestions only. This invention provides the choice of either extraction of DNA and RNA mixture or separated DNA and RNA simultaneously as well as extraction of protein from the same piece of biomaterials. It is very critical for biomaterials with limited resource, such as clinical specimens. High quality DNA, RNA and protein can be extracted from biological samples by this invention.

As flow chart shown in FIG. 1, this method performs as follows: the biological samples are homogenized in solution A containing denaturing reagents such as guanidine thiocyanate solution with neutral or high pH under cold conditions, extract the homogenate with same volume of phenol with neutral or high pH (solution B) and chloroform, and sediment by centrifugation separates the extract into three phases: aqueous phase at top, intermediate phase in the middle and organic phase at bottom. Herein the aqueous phase is named as upper phase. The inter phase and organic phase names as lower phase. Both DNA and RNA are in upper phase and can be precipitated by equal volume of isopropanol to form DNA and RNA mixture after dissolving precipitation. The DNA and RNA mixture can be used either a product for certain applications, or the mixture can be separated into separated DNA and RNA by either selective precipitation with lithium chloride (solution C) or selective enzyme digestion with RNase or DNase. Protein stays in lower phase and can be precipitated by two volumes of isopropanol. After further extraction as described detail in following, DNA, RNA and protein can be extracted simultaneously from the same piece of biomaterials.

The separated DNA and RNA can be isolated from DNA and RNA mixture by either one of two parallel selective methods as shown in FIG. 1 depending on applications of DNA or RNA. Selective precipitation of DNA and RNA mixture with lithium chloride followed by selective enzyme digesting with RNase and DNase is preferred for production of both separated DNA and RNA with excellent quality. Lithium chloride precipitates RNA selectively from DNA and RNA mixture and leaves DNA in supernatant. DNA in the supernatant can then be precipitated with isopropanol after RNA is separated apart from DNA and RNA mixture. Separated DNA and RNA then are subjected to RNase and DNase digestion respectively in case cross contamination by trace amount of DNA or RNA is a problem. Selective precipitation method produces both separated DNA and RNA with excellent quality but takes a little bit more time and effort. If only high quality of DNA is required, method of selective enzyme digestion of DNA and RNA mixture with RNase but without selective precipitation produces DNA with excellent quality but quality of RNA may be compromised by the method of selective enzyme digestion. This method takes less time and effort. Finally, protein can be extracted from lower phase as shown in FIG. 1. by isopropanol precipitation.

In an embodiment, the solution A of the present invention has a pH range of 3-10, and preferred pH is range is 7 to 10. The solution A contains denaturing reagents such as guanidine thiocyanate, β-mecapitolethanol, sodium acetate, sodium hydroxide and other reagents. The solution B contains reagents such as phenol and Chloroform. The Solution B of the present invention has a pH range of 3 to 10, and preferred pH is range is 7 to 10. The solution C contains RNA selective precipitation reagents such as lithium chloride, and buffer reagents such as Tris, sodium acetate, and etc. The solution C of the present invention has a pH range of 3 to 9, and preferred pH is range is 4 to 8.

Utilizing method in this invention, six classes of different specimens can be extracted from the same piece of biomaterials as shown in FIG. 1. they are 1) DNA and RNA mixture; 2) separated RNA by selective precipitation with or without DNase digestion afterward to eliminate the DNA contamination; 3) separated DNA by selective precipitation with or without RNase digestion afterward to eliminate the RNA contamination; 4) separated RNA by selective enzyme digestion with DNase only; 5) separated DNA by selective enzyme digestion with RNase only; 6) Protein isolated from lower phase. Extraction of DNA, RNA and protein takes about one to four hours depending on the required quality and purity of DNA, RNA and protein. The extracted RNA is suitable for reverse transcription and polymerase chain reaction (RT-PCR), mRNA isolation, gel electrophoresis, RNA protection assay, Northern analysis, RNA array, primer extension, RNA protection, cDNA synthesis, labeling, and etc. The extracted genomic DNA is suitable for enzyme digestion, gel electrophoresis, Southern analysis, PCR, sequencing, DNA array, labeling, and etc. The extracted protein is suitable for Western analysis, protein array, sequencing, immunoprecipitation, polyacrylamide gel electrophoresis, labeling, and etc. The six classes of DNA, RNA and protein extracted by reagents with high pH are as good as, or even better than, that extracted individually by other conventional methods.

To compare the method in this invention, other conventional methods to, individually or simultaneously, extract DNA, RNA and protein are served as controls. Three conventional methods used as control in this invention are: 1) the conventional method for DNA extraction (abbreviated as PK method herein) follows the protocol in Molecular Cloning, briefly as following: homogenizing tissue in DNA extraction buffer; add protease K to digest overnight; phenol extraction of protein; and recover genomic DNA by ethanol precipitation; 2) the conventional method for protein extraction (abbreviated as ND method herein) follows the protocol in Current Protocol, briefly as following: homogenizing tissue in protein extraction buffer with protease inhibitors, non-ionic detergent and buffer system, performing centrifugation of tissue homogenates, and recover supernatant as protein specimens; and 3) the conventional method for simultaneous extraction of DNA, RNA and protein (abbreviated as Kit method herein) follows the protocol of kit method for RNA extraction by reagents with low pH provided by Invitrogene as described before. Some key processes in the protocol of kit method are different from the method in this invention, such that reagents with low pH are used in the kit method, DNA is extracted from lower phase, and no lithium chloride is used to precipitate RNA in the kit method.

Difference in pH of extraction reagents between method of this invention and kit method determines how to extract DNA and protein and what quality of DNA, RNA and protein will be. As shown in FIG. 2 DNA is shifted from organic phase, after extraction by reagents with low pH, to aqueous phase after extraction with high pH reagents as shown in lane 3 and lane 6. Extraction by reagents with high pH yields more DNA and RNA than extraction by reagents with low pH as shown in lane 6 and lane 7 compared to lane 3 and lane 2. DNA heavily contaminates protein after extraction by reagents with low pH, and DNA sticks in gel well during gel electrophoresis as shown in lane 5. As shown in FIG. 6 yield of protein is lower and entirety of protein population is less complete in protein extracted by reagents with low pH as shown in lane 3 than protein extracted by reagents with high pH as shown in lane 4. Thus, DNA, RNA and protein extracted by reagents with low pH in Kit method have lower yield and heavier contamination partially because extraction by reagents with low pH moves most DNA and some RNA into organic phase.

Agarose gel electrophoresis of DNA and RNA is performed to examine the content and intactness of DNA and RNA extracted by reagents with high pH in this invention, by protease K digestion method for DNA extraction and by reagents with low pH in kit method for RNA extraction. DNA and RNA mixture as specimen referred as class 1 contain both DNA and RNA. Gel electrophoresis of DNA and RNA mixture has confirmed that there are both DNA and RNA in this mixture as shown in FIG. 3. Separated RNA and DNA from DNA and RNA mixture by selective precipitation are specimens referred as class 2 and 3. It can be successfully isolated without contamination of RNA or DNA respectively. The quality of DNA extracted by reagents with high pH and selective precipitation in this invention is similar as that extracted by protease K digestion method as shown in lane 1 and 2, FIG. 4, and is much better than that extracted by reagents with low pH as shown in FIGS. 10, 12 and 13. The quality of RNA extracted by reagents with high pH and selective precipitation in this invention is better than that extracted by reagents with low pH in kit method as shown in FIGS. 4, 8, 9, 10, and 11. Hybridization of RNA after gel electrophoresis and transferring RNA to membrane is another test for intactness of RNA. As shown in Panel B of FIG. 8, RNA extracted by reagents with high pH and selective precipitation in this invention presents no degradation of RNA and fitness for hybridization. Thus DNA extracted by reagents with high pH possesses the same quality as that extracted by conventional method for DNA extraction. DNA and RNA extracted by reagents with high pH possess the superior quality than that extracted by reagents with low pH in kit method.

Separated DNA from DNA and RNA mixture by selective enzyme digestion is specimen referred as class 4 that shows similar quality in FIG. 5 as that extracted by reagents with high pH and selective precipitation methods shown in FIG. 4, while as specimen class 5, separated RNA from DNA and RNA mixture by selective enzyme digestion shows compromised quality in FIG. 5 compared with that extracted by reagents with high pH and selective precipitation methods shown in FIG. 4. RNA extracted by reagents with low pH as Kit method shows much compromised quality after it was treated with DNase in comparison with RNA extracted by reagents with high pH and selective precipitation methods shown in lane 2 and lane 1, FIG. 11. Thus the quality of separated DNA from DNA and RNA mixture by selective enzyme digestion has good quality for any applications, and the quality of separated RNA from DNA and RNA mixture by selective enzyme digestion is compromised.

SDS-Polyacrylamide Gel Electrophoresis (SDS-PAGE) of protein is performed to examine the content and intactness of protein extracted by reagents with high pH in this invention, by reagents with low pH in kit method, and by non-ionic detergents in conventional method. Western analysis is followed afterward. As shown in FIG. 6, more amount and complete entirety of protein as shown in lane 4 is extracted by reagents with high pH in this invention than protein extracted by reagents with low pH in kit method as shown in lane 3, Panel A; and that intensity of GAPDH signal in Western blot analysis of protein extracted by reagents with high pH as shown in lane 4 is much stronger than protein extracted by reagents with low pH as shown in lane 3, Panel B. Data in FIG. 6 also indicated that similar amount and entirety of protein population as shown in lane 4 is extracted by reagents with high pH as protein extracted by non-ionic detergent in conventional methods but without extraction by organic reagents as shown in lane 2, Panel A; and that intensity of GAPDH signal in Western blot analysis of protein extracted by reagents with high pH as shown in lane 4 is similar as the protein extracted by non-ionic detergent methods as shown in lane 2, Panel B. Band patterns of protein specimens are the same although the two specimens of protein are isolated by different methods as shown in lane 2 and lane 4, which indicated that proteins are intact and entirety of protein population is complete with correct size range. Thus, protein extracted by reagents with high pH in this invention has similar yield and signal in Western analysis as protein extracted by non-ionic detergent in conventional method. Protein extracted by reagents with high pH in this invention has higher yield and stronger signal in Western analysis than protein extracted by reagents with low pH in kit method.

Polymerase Chain Reaction (PCR) or Reverse Transcription PCR (RT-PCR) PCR) of DNA and RNA serve as method to examine either the functions of DNA and RNA as fitness for application of PCR or RT-PCR, or the contamination of trace amounts of RNA or DNA in isolated DNA and RNA specimens respectively. As shown in Panel A of FIG. 7, DNA and RNA contained in DNA and RNA mixture are functioned very well for PCR and RT-PCR. Separated DNA and RNA isolated by selective precipitation method with further enzyme digestion are functioned very well for PCR and RT-PCR respectively without contamination of RNA and DNA as shown in Panel B of FIG. 6. Separated DNA and RNA isolated by selective enzyme digestion method are functioned very well also for PCR and RT-PCR respectively without contamination of RNA and DNA as shown in Panel C of FIG. 7. Therefore, DNA and RNA mixture, separated DNA and RNA extracted by this invention function very well in PCR or RT-PCR as extracted by other method. Contamination of DNA or RNA can be eliminated.

Representation or entirety in populations of RNA is evaluated by two methods: 1) identification of RNA populations with extra large size by gel electrophoresis; and 2) cDNA synthesis from RNA and identification of cDNA populations with extra large size by gel electrophoresis of synthesized cDNA from the RNA. As shown in Panel A of FIG. 8, RNA extracted by reagents with high pH and selective precipitation shows extra populations of RNA with extra large size in lane 1, Panel A of FIG. 8; compared with the RNA extracted by reagents with low pH in Kit method as shown in lane 2. This is confirmed by the examination of cDNA synthesis. As shown in Panel A and B of FIG. 9, extra populations of cDNA with extra large size is synthesized from RNA extracted by reagents with high pH and selective precipitation in this invention; compared with RNA extracted by reagents with low pH in kit method. Therefore, RNA extracted by reagents with high pH in this invention possesses more complete representation or entirety in populations of RNA than RNA extracted by reagents with low pH in kit method.

Cross contamination by protein and DNA is the major problem for DNA, RNA and protein extracted by reagents with low pH. DNA (from lower phase) and RNA (from upper phase) extracted by reagents with low pH are contaminated with protein as shown in lane 1 and 2, FIG. 10 but not the DNA (from upper phase) and RNA (from upper phase) extracted by reagents with high pH as shown in lane 4 and 5, FIG. 10. DNA contaminates protein extracted by reagents with low pH heavily as shown in lane 5 but not that much in protein extracted by reagents with high pH in lane 10, FIG. 2. The reason for protein contamination in RNA extracted by reagents with low pH is that organic phase can dissolve into aqueous phase in extraction by reagents with low pH as shown in Table 1. The volume of organic phase takes about 2% of volume of aqueous phase. Thus the volume of organic phase dissolved in aqueous phase is about 2% organic phase assuming that volume of aqueous phase is similar as organic phase, and RNA in aqueous phase could be contaminated by 2% of total protein dissolved in organic phase. The reason for protein contamination in DNA extracted from lower phase by reagents with low pH is rather obvious because DNA is precipitate by ethanol from lower phase where huge amount of protein exists. Contaminated protein in DNA is co-precipitated by ethanol precipitation of DNA from huge amount of protein while ethanol is as effective denaturing reagent to precipitate protein too. The reason for DNA contamination in protein extracted from lower phase by reagents with low pH is even more obvious as most DNA moves into organic phase during extraction by reagents with low pH. It is reasonable to believe that DNA and RNA extracted by reagents with low pH in kit method are susceptible to be contaminated by protein; and DNA and RNA extracted by reagents with high pH have less possibility to be contaminated by protein.

TABLE 1

Upper (Aqueous) Phase Contaminated by lower (Organic) Phase
during Extraction by Reagents with Low pH
Homogenate and extract cell line by reagents (Guanidine-TC and
phenol) with low or high pH.
Take upper phase 1 ml each to carry on following test

| pH of Phenol | 4.3 | 9.5 |
|---|---|---|
| Volume of upper phase | 1 ml | 1 ml |
| Add NaOH 10 N, 1 to 30 µl | Clear | Clear |
| 40 µl NaOH | Cloud | Cloud |
| Spin 5 min at 10,000 RPM in micro centrifuge | 20 µl organic phase at bottom of tube | No organic phase |
| 60 µl NaOH | No organic phase | Some precipitation |
| 80 µl NaOH | No organic phase | Some precipitation |
| 100 µl NaOH | No organic phase | Some precipitation |

1. Organic phase is dissolved in to aqueous phase as 2% volume of aqueous phase if extracted by reagents with low pH.
2. No organic phase is dissolved in to aqueous phase if extracted by reagents with neutral or slightly high pH.
3. Organic phase goes back to aqueous phase if extracted by reagents with extreme high pH.

Table 1 shows the process and results to determine that aqueous phase is contaminated by organic phase during extraction of biological samples by organic reagents with low pH.

Protein contamination in RNA and DNA is the fatal defect of RNA or DNA extracted by reagents with low pH in kit method. Due to contamination by protein or RNase, RNA extracted by reagents with low pH is more susceptible to be degraded than RNA extracted by reagents with high pH under non-denaturing condition. This is evidenced during DNase treatment as shown in lane 1 and 2 of FIG. 11. DNA extracted from lower phase is contaminated by protein or uncharacterized materials much heavier than DNA extracted from aqueous phase, which causes that DNA extracted from lower phase cannot perform gel electrophoresis as shown in lane 4, 5 and 6 of FIG. 12. However DNA extracted from upper phase can perform gel electrophoresis very well as shown in lane 2 and 3 of FIG. 12. Therefore, there is no way for extraction by reagents with low pH to get good DNA because there is no DNA in upper phase as shown in lane 1 of FIG. 3. DNA extracted from lower phase cannot perform gel electrophoresis as shown in lane 4. The contaminants in DNA extracted from lower phase are resistant to ethanol wash and phenol extraction, prevent gel electrophoresis of DNA and restriction enzyme digestion but do not prevent contaminated DNA from digestion by DNase as shown in lane 3, 4, 5, 6 and 7 of FIG. 13. The contaminants in DNA will disassociate from DNA with present of formaldehyde since contaminated DNA can perform electrophoresis in denaturing agarose gel as shown in lane 9 of FIG. 13. The nature of contaminants in DNA extracted from lower phase is not investigated here. It can be polysaccharide, proteoglycan, lipid, and some types of protein complex. Thus protein contamination in RNA extracted by reagents with low pH in kit method causes RNA more susceptible to be degraded than RNA extracted by reagents with high pH. Contamination in DNA extracted from lower phase by reagents with low pH cannot perform common applications of DNA, such as restriction enzyme digestion and gel electrophoresis.

The methods to extract DNA, RNA and protein simultaneously from biomaterials in this invention have been optimized through many different and well-controlled experiments. Table 2 shows some of data from these experiments. These data support that methods in this invention is the optimum methods to extract DNA, RNA and protein simultaneously from biomaterials. Table 3 shows the summary of yields of DNA, RNA and protein extracted by reagents with different pH. Data indicated that extraction by reagents with high pH has higher yield of genomic DNA, RNA and protein than conventional methods, such as extraction by reagents with low pH in kit method, extraction by protease K digestion for DNA, and extraction by non-ionic detergent for protein. Table 4 shows the comparison among different methods for extracting DNA, RNA and Protein. Eighteen parameters are thoroughly examined and compared to reflect properties of DNA, RNA and protein extracted by reagents with high pH, extracted by reagents with low pH, extracted by protease K digestion, and extracted by non-ionic detergents. Data indicated that the methods to extract DNA, RNA and protein simultaneously from biomaterials in this invention are the best methods to extract DNA, RNA and protein simultaneously from biomaterials among any methods available.

In the methods to extract DNA, RNA and protein by reagents with high pH in this invention, majority of DNA and RNA are existed at upper (aqueous) phase, inter phase contains only a very small portion of DNA and RNA, and organic phase contains trace amount of DNA and RNA from biomaterials. In contrary, in the methods to extract DNA, RNA and protein by reagents with low pH in kit method, majority of DNA and some of RNA are moved into lower phase whereas some protein is moved into upper phase alone with organic phase dissolving into aqueous. Majority of protein are existed at inter and organic phase, and inter phase contains different populations of proteins from that contained in organic phase in both methods. Different distributions of DNA, RNA and protein in aqueous phase, inter phase and organic phase between methods in this invention and in commercial kit method cause discrepancy of yield, purity, quality and performance of DNA, RNA and protein extracted by these two methods.

TABLE 2

Optimization for Extraction of DNA, RNA and Protein

| Data Set 1 | | DNA | | | RNA | | | mRNA | | |
|---|---|---|---|---|---|---|---|---|---|---|
| Phase | Phenol pH | LiCl 4.3 | LiCl 7.0 | Pro Con | LiCl 4.3 | LiCl 7.0 | Pro Con | LiCl 4.3 | LiCl 7.0 | DNA Con |
| Aqueous | Phe/Chl | 1360 | 1466 | ++ | 3030 | 2950 | + | 27.2 | 26.4 | ++ |
| Phase | High pH | 1410 | 1286 | − | 3420 | 3400 | − | 25.6 | 25.7 | ++ |
| (Yield µg/g | Neutral | 963 | 973 | − | 2860 | 2850 | − | 26 | 22.6 | ++ |
| tissue) | Low pH | 804 | 797 | + | 3370 | 2200 | ++ | 17.4 | 16 | + |

| Data Set 2 | | DNA | | | RNA | | | Protein | | |
|---|---|---|---|---|---|---|---|---|---|---|
| Phase | Phenol pH | SDS | Eth Ppt | Pro Con | SDS | Eth Ppt | Pro Con | Isop only | Eth Isop | DNA Con |
| Inter | Phe/Chl | 7.6 | NA | NA | Er | NA | NA | NA | NA | NA |
| phase | High pH | 29.5 | 393 | − | 13.0 | NA | − | 29 mg | 29 mg | No |
| (Yield µg/g | Neutral | 18.9 | 542 | + | 3.0 | NA | + | 29 mg | 29 mg | No |
| tissue) | Low pH | 17.2 | 564 | ++ | 7.3 | NA | ++ | 13 mg | 13 mg | Yes |
| Organic | Phe/Chl | 0 | NA | NA | 0 | NA | NA | NA | NA | NA |
| Phase | High pH | 0 | 11.1 | − | 0 | NA | NA | 20 mg | 20 mg | No |
| (Yield µg/g | Neutral | 0 | 13.3 | + | 0 | NA | NA | 20 mg | 20 mg | No |
| tissue) | Low pH | 0 | 1.1 | ++ | 0 | NA | NA | 9 mg | 9 mg | Yes |

| Yield Summary | | DNA | | | RNA | | | Protein | | |
|---|---|---|---|---|---|---|---|---|---|---|
| Yield | Phenol pH | Aque. Phase | Inter Phase | Total | Aque. Phase | Inter Phase | Total | Inter Phase | Organic Phase | Total |
| Yield µg/g | Phe/Chl | 1410 | NA | | 2990 | NA | | 29 mg | 20 mg | 49 mg |
| tissue in | High pH | 1350 | 393 | 1743 | 3410 | 13 | 3423 | 29 mg | 20 mg | 49 mg |
| aqueous, | Neutral | 970 | 542 | 1512 | 2855 | 3 | 2858 | 29 mg | 20 mg | 49 mg |
| inter and organic phases | Low pH | 800 | 564 | 1364 | 2785 | 7.3 | 2792 | 13 mg | 9 mg | 22 mg |
| Percentage | Phe/Chl | NA | NA | NA | NA | NA | NA | 59 | 41 | 100 |
| (%) in | High pH | 77 | 23 | 100 | 99.6 | 0.4 | 100 | 59 | 41 | 100 |
| aqueous, | Neutral | 64 | 36 | 100 (87*) | 99.9 | 0.1 | 100 (84*) | 59 | 41 | 100 (100*) |
| inter and organic phases | Low pH | 59 | 41 | 100 (78*) | 99.7 | 0.3 | 100 (82*) | 59 | 41 | 100 (45*) |

*Percentage to the value of High pH

Table 2 shows some data from many different and well-controlled experiments for optimization of the method to extract DNA, RNA and protein simultaneously from biomaterials. These data support that methods in this invention is the optimum methods to extract DNA, RNA and protein simultaneously from biomaterials. Phe/Chl stands for Phenol and Chloroform mixture in 1 to 1 ratio; Pro for protein; Con for contamination; Eth for ethanol; Ppt for precipitation; and Isop for isopropanol.

TABLE 3

Comparison of Yield and Percentage of DNA, RNA and Protein at Different Phases of Extraction by Reagents with Different pH and Different Methods

| | | DNA (µg/g) | | RNA (µg/g) | | Protein (mg/g) | |
|---|---|---|---|---|---|---|---|
| Phases | Phenol pH | DrP | PK | DrP | Kit | DrP | ND |
| | | Comparison of Yield | | | | | |
| Upper | High pH | 1875 | | 3460 | | − | |
| (Aqueous) | Neutral | 1400 | 1000 | 3170 | | − | 45 |
| Phase | Low pH | 875 | | 3280 | 3000 | + | NA |
| Lower (Inter | High pH | 180 | NA | 13 | NA | 49 | NA |
| and Organic) | Neutral | 865 | NA | 3 | NA | 49 | NA |
| Phase | Low pH | 925 | NA | 73 | NA | 22 | NA |

TABLE 3-continued

Comparison of Yield and Percentage of DNA, RNA and Protein at Different Phases of Extraction by Reagents with Different pH and Different Methods

| | | DNA (µg/g) | | RNA (µg/g) | | Protein (mg/g) | |
|---|---|---|---|---|---|---|---|
| Phases | Phenol pH | DrP | PK | DrP | Kit | DrP | ND |
| | | Comparison of Percentage (High pH as 100%) | | | | | |
| Upper | High pH | 100 | | 100 | | − | |
| (Aqueous) | Neutral | 75 | 53 | 92 | | − | 91 |
| Phase | Low pH | 47 | | 95 | 87 | + | |
| Lower (Inter | High pH | 9.6 | NA | 0.4 | NA | 100 | NA |
| and Organic) | Neutral | 46 | NA | 0.1 | NA | 100 | NA |
| Phase | Low pH | 49 | NA | 2.1 | NA | 45 | NA |

In Table 3 Drp stands for the invented methods of extracting DNA, RNA and protein by reagents with high pH herein; Kit is the kit method of extracting DNA, RNA and protein by reagents with low pH; PK is the conventional method of extracting DNA by protease K digestion; and ND is the conventional method of extracting protein by non-ionic detergent.

TABLE 4

Functional Comparison Among Different Methods for Extracting DNA, RNA and Protein

| | DrP Method in this Invention (high pH) | | | | | | | | Conventional Methods | | | | |
| | | | | | | | | | Kit extracting | | | | |
| Parameters | Non-selection (DNA and RNA Mixture) | | | Selective Precipitation | | | Selective Enzyme Digestion | | | DNA, RNA and protein at low pH | | | PK | ND |
| --- | --- | --- | --- | --- | --- | --- | --- | --- | --- | --- | --- | --- | --- | --- |
| Specimens | D | R | P | D | R | P | D | R | P | D | R | P | D | P |
| Yield (µg/g tissue) | 6921 | | 66 mg | 2432 | 2125 | 66 mg | 3631 | 3868 | 66 mg | 1230 | 1500 | 29 mg | 2550 | 60 mg |
| Purity (UV 260/280) | | 1.82 | | 1.77 | 1.97 | | 1.75 | 1.93 | | 1.70 | 1.9 | | 1.6 | |
| Intactness (DNA) | 30 K | | | 30 K | | | 30 K | | | 30 K | | | 30 K | |
| Intactness (RNA) (28S/18S Ratio) | | 1.5 | | | 1.5 | | | 1.29 | | | 1.3 | | | |
| Intactness (Protein) | | | ++ | | | ++ | | | ++ | | | + | | + |
| Entirety (Protein) | | | +++ | | | +++ | | | +++ | | | − | | ++ |
| Western | | | ++ | | | ++ | | | ++ | | | − | | ++ |
| Agilent Pattern | | +++ | +++ | | +++ | +++ | | ++ | +++ | | ++ | − | | ++ |
| Function of DNA (PCR) | ++ | ++ | − | ++ | − | − | ++ | − | − | ++ | − | + | ++ | + |
| Function of RNA (RT-PCR) | ++ | ++ | − | − | ++ | − | − | ++ | − | − | ++ | − | − | − |
| RNA with extra large size | NA | ++ | − | | ++ | − | | + | − | | − | − | − | − |
| cDNA with extra large size | | ++ | − | | ++ | − | | + | − | | − | − | − | − |
| Contamination of DNA (PCR) | NA | ++ | − | NA | + | − | NA | − | − | NA | + | + | NA | + |
| Contamination of RNA (RT-PCR) | ++ | NA | − | − | NA | − | | NA | − | − | NA | − | − | − |
| Contamination of Protein (Gel) | − | − | NA | − | − | NA | − | − | NA | + | + | NA | −− | NA |
| RNA degraded in DNAse treatment | | + | | | − | | | + | | | ++ | | | |
| Electrophoresis | ++ | ++ | ++ | ++ | ++ | ++ | ++ | ++ | ++ | − | ++ | ++ | ++ | ++ |
| Hybridization | ++ | ++ | | ++ | ++ | | ++ | ++ | | − | ++ | | ++ | |

In Table 4 the methods for extracting DNA, RNA and protein in this invention are compared with conventional methods regarding to the function of extracted DNA, RNA and protein. DNA, RNA and protein are extracted from rat Liver and human spleen tissues and data in table are integrated. D, R and P stand for DNA, RNA and protein respectively. Drp stands for the invented methods of extracting DNA, RNA and protein by reagents with high pH herein; Kit is the kit method of extracting DNA, RNA and protein by reagents with low pH; PK is the conventional method of extracting DNA by protease K digestion; and ND is the conventional method of extracting protein by non-ionic detergent.

The advantages to extract DNA by reagents with high. pH are high yield and high purity. The reason for higher yield in genomic DNA is that in this invention genomic DNA is extracted from upper phase, where 90% of genomic DNA stays, due to application of reagent with high pH that moves majority of DNA into upper phase. There are only about 50% of total genomic DNA existed in inter phase and there are trace amount of DNA in organic phase when extracted by reagents with low pH. Thus, recovery efficiency of DNA from upper phase is higher as amount of DNA is richer and fewer materials interfere with DNA extracted in upper phase. To the contrary, kit method by reagents with low pH extracts genomic DNA from inter and organic phases by ethanol precipitation. Although 50% of DNA has been moved into inter and organic phases due to application of reagent with low pH, recovery efficiency of genomic DNA from these two phases is lower because DNA may be tangling together with lipid, polysaccharide, or proteoglycan. Actually inter phase contains much more genomic DNA than organic phase. Precipitations of both inter phase and organic phase for DNA extraction could be one of major reasons to contaminate DNA with other materials in organic phase as DNA may be tangling together with lipid, polysaccharide, or proteoglycan and co-precipitate also. Thus, yield, purity, quality and performance of DNA extracted by reagents with low pH in kit method are very poor compared with DNA extracted from upper phase by reagents with high pH in this invention. Accordingly, this invention provides a method to extract DNA from upper phase; and extraction of DNA from inter and organic phases as kit method instructed is not an appropriate method.

Same as DNA extract by reagents with high pH, the advantages to extract RNA by reagents with high pH are high yield and high purity also. Retrieval of RNA populations with extra large size from lower phase by increasing pH of reagents for extraction may contribute partially to the higher yield of RNA in this invention, whereas these RNA populations with extra large size trapped in lower phase in extraction by reagents with low pH are wasted in the kit method. Extraction by reagents with low pH moves not only DNA into inter and organic phases, but it also moves RNA populations with extra large molecular size with DNA into inter and organic phases, which lose the RNA population with extra large molecular size. The rationale is that extraction by reagents with low pH moves nuclear acid into organic phase in a non-selectively manner depending on the molecular size of nuclear acid.

Therefore, RNA populations with extra large molecular size that is close to the size of genomic DNA are moved into organic phase and wasted by a by-stand effect. One of the reasons for high purity of RNA extracted by reagents with high pH is that no protein is moved into upper phase alone with organic phase dissolving into aqueous to contaminate RNA whereas RNA extracted by reagents with low pH is contaminated by protein alone with organic phase dissolving into aqueous. Separation of phenol from other reagents such as Guanidine in this invention is the other reason to extract RNA with high purity due to higher efficiency of extraction than extraction with pre-mixed phenol and guanidine together in kit method, in which guanidine cannot fully break cells and denature protein such as RNase with pre-present of phenol. Retrieval of RNA populations with extra large size from lower phase, no organic phase contamination in aqueous phase, and higher efficiency of extraction are the major reasons for high yield and high purity of RNA extracted by reagents with high pH.

Most of protein is existed in inter and organic phases in both methods either in this invention or in kit method. In kit method, before precipitation of protein, inter and organic phases are required to be pre-precipitated with about 40% ethanol first in order to extract DNA from these two phases because majority of DNA stays in inter phase. Some populations of proteins are lost during this pre-precipitation. Then, proteins in inter and organic phases are precipitated again with 50% isopropanol to recover proteins left from pre-precipitation. Although losing proteins, the pre-precipitation may not be avoidable because of two major reasons: first, this is only way to get genomic DNA and second, large amount of DNA may prevent proteins isolation if precipitated with proteins. To the contrary, this invention precipitates proteins directly with isopropanol to recover proteins from inter and organic phases without losing proteins during ethanol pre-precipitation to recover DNA as did in kit method. It is not necessary to recover DNA from inter and organic phases since DNA stays at aqueous phase in the method of this invention. In addition, there are much less amount of DNA in inter and organic phases, which will not prevent protein extraction. With removing DNA and RNA existed at inter phase and organic phase by reagents with high pH, protein is easy to release from precipitation of inter and organic phase due to less interference by DNA and RNA in precipitation. Therefore, in this invention, most of DNA and RNA stay in aqueous phase and only small portion of DNA stay at inter and organic phase, whereas a lot of DNA and some of RNA stay at inter and organic phase in kit method. When precipitating with ethanol, some of protein at inter phase and organic phase may be lost during co-precipitation with large amount of DNA and RNA in kit method. Yield of protein extracted by reagents with high pH is 10% more than the yield of protein extracted by non-ionic detergents method from average of 40 different tissues and is 100% more than the yield of protein extracted by reagents with low pH. Thus, the yield of protein is much higher and entirety of protein populations is more complete by this invention than the yield and entirety of protein populations by kit method.

This invention provides methods to extract genomic DNA, RNA and protein simultaneously from the same piece of biomaterials. There are six classes of DNA, RNA and protein extracted by reagents with high pH in this invention, with the choice of either extraction of DNA and RNA mixture or separated DNA and RNA. The procedures of extraction by reagents with high pH are simplified to minimize the harsh conditions and treatments on DNA, RNA and protein molecules. The yield, purity, quality, intactness, performance and entirety of population of DNA extracted by reagents with high pH are much superior than DNA extracted by reagents with low pH, especially in higher yield of DNA (Table 3), fitness for restriction enzyme digestion and gel electrophoresis for DNA (FIG. 13), The yield, purity, quality, intactness, performance and entirety of population of RNA extracted by reagents with high pH are much superior than RNA extracted by reagents with low pH, especially in retrieving more complete entirety of RNA populations with extra large molecular size (FIGS. 8 and 9) and increasing resistance to degradation in DNase treatment of RNA (FIG. 11). The yield, purity, quality, intactness, performance and entirety of population of protein extracted by reagents with high pH are much superior than protein extracted by reagents with low pH, especially in much higher yield of protein (Table 3), retrieving more complete entirety of protein populations and stronger signal in Western blotting analysis for protein (FIG. 6). The yield, purity, quality, intactness, performance and entirety of population of DNA and protein extracted by reagents with high pH are superior or similar as DNA and protein extracted individually by other conventional methods, such as protease K digestion for DNA extraction (FIG. 4 and Table 3) and non-ionic detergent for protein extraction (FIG. 6 and Table 3). Therefore, the methods to extract DNA, RNA and protein simultaneously from biomaterials in this invention are the most optimized methods to extract DNA, RNA and protein simultaneously from biomaterials among any methods available.

There are five reasons or drawbacks for poor yield, purity, quality, intactness, performance and entirety of population of DNA, RNA and protein extracted by kit method. Extraction by reagents with low pH in kit method is responsible for four reasons or drawbacks, it are: 1) moving DNA and RNA populations with large size into lower phase as FIGS. 2, 8 and 9 indicated; 2) extraction of DNA from wrong (lower) phase of extraction as FIGS. 2 and 13 indicated; 3) RNA and DNA more susceptible to be contaminated by protein as FIG. 10 and Table 1 indicated; and 4) protein contaminated by DNA as FIG. 2 indicated. The fifth reason or drawback is that extraction by pre-mixed phenol and guanidine with low pH as used in kit method decreases the efficiency of extraction because guanidine cannot completely break cells and denature protein such as RNase with pre-present of phenol. Kit method has all of the five reasons or drawbacks for poor yield, purity, quality, intactness, performance and entirety of population of DNA, RNA and protein because it extracts DNA, RNA and protein by pre-mixed guanidine and phenol with low pH.

Procedures to extract DNA, RNA and protein in this invention have corrected the aforementioned five drawbacks through two important processes, A) extraction by reagents with high pH and B) separation of phenol from guanidine in extraction solution. A) Extraction by reagents with high pH increases yield of DNA, RNA and protein and prevents DNA, RNA and protein from contamination through following mechanisms: 1) moving DNA and RNA populations with extra large size into upper phase to increase yield of DNA and RNA as FIGS. 2, 8, 9, 12 and Table 3 indicated, 2) extracting DNA from upper phase instead of lower phase to increase yield and prevent DNA from contamination by protein in lower phase as FIGS. 2, 13 and Table 3 indicated, 3) eliminating contamination by lower phase into upper phase to prevent RNA and DNA from contamination by protein dissolved in lower phase as FIG. 10, Table 1 and FIG. 11 indicated, and 4) by purging DNA from lower phase into upper phase to prevent protein from contamination by DNA as FIG. 2 indicated. B) Separation of phenol from guanidine in extraction solution increases the efficiency of denaturing protein and extracting protein from upper phase to improve the yield and quality of DNA, RNA and protein. Thus, the method in this invention have corrected the poor yield, purity, quality, intactness, performance and entirety of population of DNA, RNA and protein extracted by reagents with low pH in kit method through extraction by reagents with high pH to relocate DNA and RNA and to eliminate contamination, and separation of phenol from guanidine in extraction solution to increase the efficiency of extraction.

In summary, methods in this invention extract genomic DNA, RNA and protein simultaneously from the same piece of biomaterials. There are six classes of DNA, RNA and protein extracted by reagents with high pH in this invention, with the choice of either extraction of DNA and RNA mixture or separated DNA and RNA. The yield, purity, quality, intactness, performance and entirety of population of DNA, RNA and protein extracted by reagents with high pH are much superior than DNA, RNA and protein extracted by reagents with low pH in kit method, especially in higher yield of DNA (Table 3), fitness for restriction enzyme digestion and gel electrophoresis for DNA (FIG. 13), retrieving more complete entirety of RNA populations with extra large molecular size (FIGS. 8 and 9) and increasing resistance to degradation in DNase treatment of RNA (FIG. 11), and much higher yield of protein (Table 3), retrieving more complete entirety of protein populations and stronger signal in Western blotting analysis for protein (FIG. 6). The method in this invention have corrected the poor yield, purity, quality and performance of DNA, RNA and protein extracted by reagents with low pH through extraction by reagents with high pH to relocate DNA and RNA and to eliminate contamination, and separation of phenol from guanidine in extraction solution to increase the efficiency of extraction. Therefore, the methods to extract DNA, RNA and protein simultaneously from biomaterials in this invention are the most optimized methods to extract DNA, RNA and protein simultaneously from biomaterials among any methods available.

EXAMPLE 1

Extract DNA, RNA and Protein Simultaneously from Biological Samples DNA, RNA and Protein are extracted simultaneously from biological samples by following flow chart in FIG. 1. For example, 1 g of a tissue sample from human liver is homogenized in 10 ml Solution A in cold condition. Solution A contains 3.8 M of guanidine thiocyanate salt (Sigma); 24 mM of Sodium Citrate, pH 7.0 to 10 (Fisher); 16 mM sarkosyl (Sigma); and 107 mM of beta-mercaptoethanol. Thereafter, 10 ml phenol saturated by 0.1 M Tris-HCl (pH 7.0 to 10) and 4 ml chloroform are added and mixed thoroughly with the homogenate. Centrifuge the mixture at 11,000 rpm for 15 minutes. Following the centrifugation, an aqueous phase containing intact RNA and DNA as shown in lane 6 and 7 of FIG. 2, an inter phase and an organic phase containing proteins are formed. 10 ml aqueous phase is collected and combined with 10 ml of isopropanol, while as 10 ml inter phase and organic phase is collected for protein isolation. The precipitate from aqueous phase containing total RNA and DNA is washed with 10 ml of 70% ethanol, centrifuged at 7,500 rpm for 10 minutes, and dissolved in water as DNA and RNA mixture according to the method described in Example 2. Separated DNA and RNA are separated according to the method described in Example 3 or Example 4. Protein is precipitated from inter phase and organic phase according to the method described in Example 5. Six classes of different specimens can be extracted from the same piece of biomaterials as shown in FIG. 1. It are 1) DNA and RNA mixture; 2) separated RNA by selective precipitation with or without DNase digestion afterward to eliminate the DNA contamination; 3) separated DNA by selective precipitation with or without RNase digestion afterward to eliminate the RNA contamination; 4) separated RNA by selective enzyme digestion with DNase only; 5) separated DNA by selective enzyme digestion with RNase only; 6) Protein isolated from lower phase. Extraction of DNA, RNA and protein will take about one to four hours depending on the required quality and purity of DNA, RNA and protein. The yield, purity, quality, intactness, performance and entirety of population of DNA, RNA and protein extracted by reagents with high pH are much superior than DNA, RNA and protein extracted by reagents with low pH in kit method as shown in FIGS. 4, 6 and Table 4

EXAMPLE 2

DNA and RNA in DNA and RNA mixture is isolated together without separation each other. For example, 1 g of a tissue sample from human liver is homogenized in 10 ml Solution A in cold condition. The precipitate from aqueous phase containing total RNA and DNA is washed with 10 ml of 70% ethanol, centrifuged at 7,500 rpm for 10 minutes according to the method described in Example 1. The pellet containing total RNA and DNA is dissolved in water as DNA and RNA mixture. The isolation of mixture of RNA and DNA as described takes about one and half hour.

Image of DNA and RNA mixture in gel electrophoresis is shown in FIG. 3. In denaturing agarose gel electrophoresis as show in Panel A of FIG. 3, both RNA and DNA are not degraded, thus intact RNA and DNA can be visualized in gel, which indicates that there are both intact RNA and DNA in DNA and RNA mixture. DNA gel shown in Panel B of FIG. 3 further confirms the fact that there are intact DNA in DNA and RNA mixture.

EXAMPLE 3

Separated DNA and RNA are separated by selective precipitation of DNA and RNA mixture prepared in example 2. The precipitate from aqueous phase containing total RNA and DNA in example 2 is dissolved in water as DNA and RNA mixture. 7.5M Lithium Chloride is added into DNA and RNA mixture to precipitate RNA selectively, in which final concentration of Lithium Chloride is 2.5M. DNA and RNA mixture with 2.5M Lithium Chloride is stored at −80° for one hour and centrifuged at 11,000 rpm for 30 minutes. The precipitate containing RNA is washed with 70% ethanol twice and then dissolved in water as separated RNA. The supernatant containing genomic DNA is precipitated with the same volume of isopropanol at −80° for one hour and centrifuged at 11,000 rpm for 30 minutes. The precipitate containing DNA is washed with 70% ethanol twice and then dissolved in water as separated DNA. The separated RNA or DNA is undergone DNase or RNase digestion respectively to get rid of DNA or RNA contaminations in respective specimens. Enzyme digested RNA or DNA is extracted by phenol and precipitated with same volume of isopropanol at −80° C. for one hour and centrifuged at 11,000 rpm for 30 minutes. Resulting precipitates containing separated RNA or DNA are dissolved in water as final separated RNA or DNA specimens.

Image of separated RNA and DNA isolated by selective precipitation on gel electrophoresis is shown in FIG. 4. In non-denaturing agarose gel electrophoresis as show in Panel A of FIG. 4, DNA are not degraded compared with conventional protease K digestion method, thus intact DNA can be visualized in gel, which indicates that there is intact DNA in separated DNA specimens. Electrophoresis of RNA in denaturing agarose gel as shown in Panel B of FIG. 3 confirms that RNA is intact in separated RNA specimens compared with conventional method.

EXAMPLE 4

Separated DNA and RNA are separated by selective enzyme digestion of DNA and RNA mixture prepared in example 2. The precipitate from aqueous phase containing total RNA and DNA in example 2 is dissolved in water as DNA and RNA mixture and divided into two portions. Either DNase or RNase in an appropriate concentration, such as 1 unit of enzyme per microgram DNA and RNA, is added into one portion of DNA and RNA mixture to digest either DNA or RNA selectively. Digestion takes about one to two hour at 37° C. Enzyme digested RNA or DNA are extracted by phenol and precipitated with same volume of isopropanol at −80° C. for one hour and centrifuged at 11,000 rpm for 30 minutes. Resulting precipitates containing RNA or DNA are dissolved in water as final separated RNA or DNA specimens.

Image of separated RNA and DNA isolated by selective enzyme digestion on gel electrophoresis is shown in FIG. 5. In non-denaturing agarose gel electrophoresis as show in lane 1 of FIG. 5, DNA is not degraded, thus intact DNA can be visualized in gel, which indicates that there is intact DNA in separated DNA specimens. Electrophoresis of DNA in denaturing agarose gel as shown in lane 2 of FIG. 5 confirms that DNA is not contaminated by large size RNA. Electrophoresis RNA in denaturing agarose gel shown in lane 3 of FIG. 5 confirms that RNA is intact in separated RNA specimens. Electrophoresis of RNA in non-denaturing agarose gel as shown in lane 4 of FIG. 5 confirms that RNA is not contaminated by DNA.

EXAMPLE 5

Protein is extracted from inter phase and organic phase in Example 1. Ethanol in 0.6 volume of inter phase and organic phase is added into inter phase and organic phase at 38% concentration to pre-precipitated materials that affect extraction of protein afterward, such as rest of DNA and RNA, and other materials in inter phase and organic phase. After centrifugation at 3500 rpm for 10 minutes, precipitate can be used for extraction of DNA if necessary, and supernatant is precipitated for isolation of protein. The pre-precipitation by ethanol can be omitted if extracted by reagents with high pH. The protein contained in the resulting supernatant is precipitated with 75% of isopropanol by combining the supernatant with 3 volumes of isopropanol and centrifuging at 11,000 rpm for 15 minutes. The resulting precipitate containing protein is washed with 20 ml of 95% ethanol with 0.3M guanidine hydrochloride (kit method) or with 100% ethanol only for 3 times, and dissolve in 1% SDS. To increase the recovery efficiency of protein, precipitate containing protein is broken into small pieces. After centrifuging at 11,000 rpm for 15 minutes, supernatant containing protein is recovered.

SDS-Polyacrylamide gel electrophoresis is performed with protein recovered from inter phase and organic phase. Protein is intact in SDS-Polyacrylamide gel electrophoresis. More amount and entirety of protein is extracted by reagents with high pH as shown in lane 4 of Pane A in FIG. 6 than protein extracted by reagents with low pH as shown in lane 3 of Panel A; and that intensity of GAPDH signal in Western blot analysis of protein extracted by reagents with high pH as shown in lane 4 of Panel B is much stronger than protein extracted by reagents with low pH as shown in lane 3 of Panel B. Data also indicated that similar amount and entirety of protein is extracted by reagents with high pH as protein extracted by conventional methods with non-ionic detergent but without extraction by organic reagents as shown in lane 2 of Panel A; and that intensity of GAPDH signal in Western blot analysis of protein extracted by reagents with high pH is similar as the protein extracted by conventional methods as shown in lane 2 of Panel B. Proteins are not degraded and display the different bands in gel.

EXAMPLE 6

The yield, purity, quality, intactness, performance and entirety of population of DNA, RNA and protein extracted by reagents with high pH are much superior than DNA, RNA and protein extracted by reagents with low pH in kit method, especially in higher yield of DNA (Table 3), fitness for restriction enzyme digestion and gel electrophoresis for DNA (FIG. 13), retrieving more complete entirety of RNA populations with extra large molecular size (FIGS. 8 and 9) and increasing resistance to degradation in DNase treatment of RNA (FIG. 11), and much higher yield of protein (Table 3), retrieving more complete entirety of protein populations and stronger signal in Western blotting analysis for protein (FIG. 6). The yield, purity, quality, intactness, performance and entirety of population of DNA and protein extracted by reagents with high pH are superior or similar as DNA and protein extracted individually by other conventional methods, such as protease K digestion for DNA extraction (FIG. 4 and Table 3) and non-ionic detergent for protein extraction (FIG. 6 and Table 3).

There are five reasons or drawbacks for poor yield, purity, quality, intactness, performance and entirety of population of DNA, RNA and protein extracted by kit method. Extraction by reagents with low pH in kit method is responsible for four reasons or drawbacks, they are: 1) moving DNA and RNA populations with large size into lower phase as FIGS. 2, 8 and 9 indicated; 2) extraction of DNA from wrong (lower) phase of extraction as FIGS. 2 and 13 indicated; 3) RNA and DNA more susceptible to be contaminated by protein as FIG. 10 and Table 1 indicated; and 4) protein contaminated by DNA as FIG. 2 indicated. The fifth reason or drawback is that extraction by pre-mixed phenol and guanidine with low pH as used in kit method decrease the efficiency of extraction because guanidine cannot completely break cells and denature protein such as RNase with pre-present of phenol.

Yield and purity of DNA, RNA and protein are two important parameters to evaluate the methods for isolation of DNA, RNA and protein. Methods in this invention have higher yield in DNA, RNA and protein per gram of biomaterials compared with Kit method as shown in Table 3. The reason for higher yield in genomic DNA is that in this invention genomic DNA is extracted from aqueous phase where most of genomic DNA stays and recovery efficiency is higher. To the contrary, kit method extracts genomic DNA from organic phase where recovery efficiency of genomic DNA from organic phase is very low. Retrieval of RNA population with extra large size from organic phase by increasing pH of lower phase may contribute to the higher yield of RNA in this invention, whereas these RNA with extra large size trapped in lower phase with low pH are wasted in kit method. With less amounts of DNA and RNA interference in lower phase, protein is easy to release from precipitation of lower phase. Thus, the yield of protein is much higher in this invention compared with kit method, even higher than conventional method extracted by non-ionic detergents. Purity of RNA or DNA is higher also as compared with that in kit methods because lower phase does not contaminate upper phase when extracted by reagents with high pH and efficiency of extraction is higher when extracted by guanidine separated from phenol.

EXAMPLE 7

All six classes of specimens isolated by this invention can be used in different application depending on the purpose of testing and restriction of biomaterial resource. DNA and RNA mixture could be applied in PCR or RT-PCR as shown in FIG. 7 to identify changes in both DNA and RNA when resource of biomaterial is limited, or a high throughput testing is required. Separated DNA or RNA either by selective precipitation or by selective enzyme digestion could be applied in any routine or special applications that require pure DNA or RNA, such as RNA for reverse transcription and polymerase chain reaction (RT-PCR), mRNA isolation, gel electrophoresis of RNA, RNA protection assay, Northern analysis, RNA array, primer extension, cDNA synthesis as shown in FIGS. 7, 8, and 9, and DNA for enzyme digestion, gel electrophoresis, Southern analysis, PCR, sequencing, DNA array, and etc as shown in FIGS. 7, 12, and 13. Proteins could be applied in most routine or special applications that require pure proteins such as Western analysis, protein array, sequencing, polyacrylamide gel electrophoresis, immuno-precipitation, and etc as shown in FIG. 6.

DNA extracted by this invention can be used in any applications that require DNA with high quality, such as enzyme digestion, gel electrophoresis, Southern analysis, PCR, sequencing, DNA array, and etc. But DNA extracted by kit method from lower phase cannot be used in enzyme digestion, gel electrophoresis, thus Southern analysis as shown in FIGS. 12 and 13. Literally, kit method cannot extract DNA from biomaterials for a reasonable application.

RNA with extra large size is an extraordinary feature of RNA extracted by this invention compared with kit methods. Gene expression profile will be more complete with the population of RNA with extra large size in profiling analysis such as microarray. Northern blot made from RNA with extra large size will reveal the extra population of RNA, which is not detectable by conventional methods. cDNA library made from RNA with extra large size will contain the gene with extra large size which is not obtainable by conventional methods. Best of all, RNA with extra large size retrieve the information missed by RNA isolated by conventional method, which is crucial in development of disease or maintenance function of life, such as Epidermal Growth Factor Receptor mRNA (more that 10 kb and related to tumor development) or Titin gene (more than 100 kb and related to contraction of muscle).

Protein with much more complete entirety of population also is an extraordinary feature of protein extracted by this invention compared with kit methods as shown in FIG. 6. Protein extracted by reagents with high pH in this invention has higher yield than and similar populations of the protein extracted by conventional non-ionic detergent method, which indicated that protein extracted by this invention can be used in any applications where protein extracted by conventional methods can be used. Protein extracted by reagents with low pH in kit method only has very few or limited populations of protein compared with protein extracted by conventional method as shown in FIG. 6, which indicated that protein extracted by reagents with high pH cannot be used in most applications that require representative population of protein. Thus, literally kit method cannot extract protein from biomaterials for a reasonable application.

One of the best features in extracting specimens by this invention is that all specimens originate from the same materials. This will ensure the accuracy of data from DNA to RNA and to protein by avoiding bias introduced by donor difference, such as DNA from one donor and RNA or protein from another donor, which is very important in study of relationship among DNA, RNA and protein such as gene regulation. The another best feature is that this methods will save ⅔ of biomaterial as DNA, RNA and protein have not to be isolated from different pieces of same biomaterials, especially when resource of biomaterials is limited, such as clinical samples, while DNA, RNA or protein have to be evaluated simultaneously.

In summary, this invention presents a set of methods to extract DNA, RNA and protein simultaneously from biomaterials by reagents with high pH. DNA and RNA can be extracted from upper (aqueous) phase simultaneously either together as a DNA and RNA mixture or separated DNA and RNA. Protein can be extracted from lower (inter phase and organic phase) phases. The DNA and RNA mixture can be used either as DNA or RNA directly depending on applications without further separation, or as resource for the separated DNA and RNA that can be selected from the DNA and RNA mixture by selective precipitation and/or by selective enzyme digestions. A product is developed based on this method. The product contains extraction reagents for DNA, RNA and protein, selective precipitation reagents and/or selective digestion reagents. This invention provides the choice of extraction either of DNA and RNA mixture or of separated DNA and RNA simultaneously, as well as extraction of protein from the same piece of biomaterials, which is very critical for biomaterials with limited resource, such as clinical specimens. High quality DNA, RNA and protein can be extracted from biomaterials by this invention.

The invention has been described using exemplary preferred embodiments. However, for those skilled in this field, the preferred embodiments can be easily adapted and modified to suit additional applications without departing from the spirit and scope of this invention. Thus, it is to be understood that the scope of the invention is not limited to the disclosed embodiments. On the contrary, it is intended to cover various modifications and similar arrangements based upon the same operating principle. The scope of the claims, therefore, should be accorded the broadest interpretations so as to encompass all such modifications and similar arrangements.

We claim:

1. A method of isolating DNA, RNA and protein simultaneously from biological samples comprises:
   a) extracting DNA, RNA and protein simultaneously from the biological samples with extracting solutions comprising pH from 9.5 to 10.5 extraction reagent, wherein the extraction reagent comprising phenol and a buffer with pH from 9.5 to 10.5;
   b) separating the solutions containing said DNA, RNA and protein from step a) into an upper aqueous phase, a lower organic phase and an inter-phase there between to recover a DNA and RNA mixture from the upper aqueous phase, wherein said DNA and RNA mixture is substantially protein-free, and said upper aqueous phase has pH about 9.5 to 10.5;
   c) separating the DNA and RNA mixture into separated DNA and RNA by selective precipitation and/or selective enzyme digestions;
   d) recovering the separated DNA and RNA for applications;

e) extracting protein from the lower phase wherein said protein is substantially free of DNA and RNA; and f) Obtaining six classes of different specimens wherein said specimens are DNA and RNA mixture; substantially pure RNA without undergoing DNase treatment; substantially pure DNA without undergoing RNase treatment; substantially pure RNA obtained after DNase treatment; substantially pure DNA obtained after RNase treatment; and protein pool with full representing population of different proteins contained in said biological samples.

2. The method of claim 1, wherein the DNA and RNA mixture from step b) is ready for certain applications.

3. The method of claim 1, wherein the DNA, RNA and protein can be isolated from the same piece of biological samples at the same time.

4. The method of claim 1, wherein the biological samples include, but not limited to, tissues, blood cell, body fluid, cultured cells, cellular molecules, subcellualr components; wherein the biological examples come from organisms, such as human, animal, and plant; and wherein the organisms are under different conditions such as under normal and diseased conditions.

5. The method of claim 1, wherein the DNA, RNA and protein in step a) are isolated specifically from the same piece of biological samples at the same time.

6. The method of claim 1, wherein said DNA and RNA mixture are recovered in step b) by precipitation or matrix binding.

7. The method of claim 2, wherein the certain applications include applications that can distinguish DNA or RNA by using either one of them in the applications including, but not limited to, PCR amplification of a certain gene in genomic DNA without reverse transcription of RNA, or reverse transcription or primer extension of RNA but not DNA.

8. The method of claim 1, wherein the selective precipitation in step c) refers to methods that can precipitate DNA or RNA separately, such as precipitating RNA with lithium chloride first, then precipitating DNA with isopropanol afterward.

9. The method of claim 8, wherein the pH of lithium chloride solution is about 1.0 to 9.0 with a preferred range of about 1 to 7 to achieve better extraction result.

10. The method of claim 1, wherein the selective enzyme digestions in step c) refer to the enzyme digestions that can selectively digest only DNA or only RNA such as DNase I digestion of DNA only with preservation of RNA, or RNase A digestion of RNA only with preservation of DNA.

11. The method of claim 1, wherein the inter-phase and organic phase have a neutral or alkaline pH, in which protein prefers to stay with trace or very little amount of DNA and RNA.

12. A method of isolating DNA, RNA and protein simultaneously from an identical piece of a biological sample comprises:

a) extracting DNA, RNA and protein simultaneously from the biological samples with extracting solutions comprising pH from 9.5 to 10.5 extraction reageent, wherein the extraction reagent comprising phenol and a buffer with pH from 9.5 to 10.5;

b) separating the solutions containing said DNA, RNA and protein from step a) into an upper aqueous phase, a lower organic phase and an inter-phase there between to recover a DNA and RNA mixture from the upper aqueous phase, wherein said DNA and RNA mixture is substantially protein-free, and said upper aqueous phase has pH about 9.5 to 10.5;

c) separating the DNA and RNA mixture into separated DNA and RNA by selective precipitation and/or selective enzyme digestions;

d) recovering the separated DNA and RNA for applications;

e) extracting protein from the lower phase wherein said protein is substantially free of DNA and RNA; and f) Obtaining six classes of different specimens wherein said specimens are DNA and RNA mixture; substantially pure RNA without undergoing DNase treatment; substantially pure DNA without undergoing kNase treatment; substantially pure RNA obtained after DNase treatment; substantially pure DNA obtained after RNase treatment; and protein pool with frill representing population of different proteins contained in said biological samples.

13. A method of isolating DNA and RNA simultaneously from a biological sample substantially protein-free amenable for certain applications comprises:

a) extracting DNA, RNA and protein simultaneously from the biological samples with extracting solutions comprising pH from 9.5 to 10.5 extraction reagent, wherein the extraction reagent comprising phenol and a buffer with pH from 9.5 to 10.5:

b) separating the solutions containing said DNA, RNA and protein from step a) into an upper aqueous phase, a lower organic phase and an inter-phase there between to recover a DNA and RNA mixture from the upper aqueous phase, wherein said DNA and RNA mixture is substantially protein-free, and said upper aqueous phase has pH about 9.5 to 10.5;

c) separating the DNA and RNA mixture into separated DNA and RNA by selective precipitation and/or selective enzyme digestions;

d) recovering the separated DNA and RNA for applications; and e) Obtaining five classes of different specimens wherein said specimens are DNA and RNA mixture; substantially pure RNA without undergoing DNase treatment; substantially pure DNA without undergoing kNase treatment; substantially pure RNA obtained after DNase treatment; and substantially pure DNA obtained after RNase treatment.

14. A method of isolating protein simultaneously with DNA and RNA from a biological sample, whereas the protein is substantially free of DNA and/or RNA, comprises:

a) extracting DNA, RNA and protein simultaneously from the biological samples with extracting solutions comprising pH from 9.5 to 10.5 extraction reagenet, wherein the extraction reagent comprising phenol and a buffer with pH about 9.5 to 10.5;

b) separating the solutions containing said DNA, RNA and protein from step a) into an upper aqueous phase, a lower organic phase and an inter-phase there between to recover a DNA and RNA mixture from the upper aqueous phase, wherein said DNA and RNA mixture is substantially protein-free, and said upper aqueous phase has pH about 9.5 to 10.5; and c) recovering the protein by selective precipitation and/or selective enzyme digestions wherein said protein is protein pool with frill representing population of different proteins contained in said biological sample.

* * * * *